(12) United States Patent
Griffin et al.

(10) Patent No.: US 6,225,069 B1
(45) Date of Patent: May 1, 2001

(54) METHODS TO IDENTIFY GENETIC PREDISPOSITION TO ALZHEIMER'S DISEASE

(75) Inventors: W. Sue T. Griffin, Little Rock, AR (US); James A. R. Nicoll, Milngavie (GB)

(73) Assignee: The Board of Trustees of the University of Arkansas, Little Rock, AR (US)

(*) Notice: Subject to any disclaimer, the term of this patent is extended or adjusted under 35 U.S.C. 154(b) by 0 days.

(21) Appl. No.: 09/515,472

(22) Filed: Feb. 29, 2000

(51) Int. Cl.⁷ .............................. C12Q 1/68; C12P 19/34; C07H 21/04

(52) U.S. Cl. .................... 435/6; 435/91.2; 536/24.31; 536/24.33

(58) Field of Search .................... 435/6, 91.2, 810; 536/24.33, 24.31

(56) References Cited

U.S. PATENT DOCUMENTS

| | | | |
|---|---|---|---|
| 4,582,788 | 4/1986 | Erlich | 435/6 |
| 4,666,828 | 5/1987 | Gusella | 435/6 |
| 4,801,531 | 1/1989 | Frossard | 435/6 |
| 5,110,920 | 5/1992 | Erlich | 536/27 |
| 5,268,267 | 12/1993 | Smith | 435/6 |
| 5,328,829 | 7/1994 | Stashenko | 435/7.9 |
| 5,686,246 | * 11/1997 | Kornman et al. | 435/6 |

OTHER PUBLICATIONS

Barger SW, et al., Microglial activation by Alzheimer amyloid precursor protein and modulation by apolipoprotein E. *Nature* 1997;388:878–881.

Blakemore, AIF, et al., Interleukin–1 Receptor Antagonist Gene Polymorphism as a Disease Severity Factor in Systemic Lupus Erythematosus. *Arthritis & Rheumatism* 1994;37:9:1380–1385.

Breitner JCS, et al., Inverse association of anti–inflammatory treatments and Alzheimer's disease: Initial results of a con–twin control study. *Neurology* 1994;44:227–232.

Buxbaum JD, et al., Cholineric agonists and interleukin 1 regulate processing and secretion of the Alzheimer bata/A4 amyloid protein precursor. *Proc Natl Acad Sci USA* 1992;89:10075–10078.

Forloni, G., et al., Expression of amyloid precursor protein mRNAs in endothelial, neuronal and glial cells: Modulation by interleukin–1. *Mol Brain Res* 1992;16:128–134.

Goate A, et al., Segregation of a missense mutation in the amyloid precursor protein gene with familial Alzheimer's disease. *Nature* 1991;349:704–706.

Griffin WS, et al., Brain interleukin 1 and S–200 immunoreactivity are elevated in Down syndrome and Alzheimer disease. *Proc Natl Acad Sci USA* 1989;86:7611–7615.

Griffin WS, et al., Glial–Neuronal Interactions in Alzhemier's Disease: The Potential Role of a Cytokine Cycle in Disease Progression. *Brain Pathol* 1998; 8:65–72.

Griffin WS, et al., Microglial interleukin–1α expression in human head injury: correlations with neuronal and neuritic β–amyloid precursor protein expression. *Neurosci Lett* 1994; 176:133–136.

Mansfield JC, et al., Novel Genetic Association between Ulcerative Colitis and the Antiinflammatory Cytokine Interleukin–1 Receptor Antagonist. *Gastroenterology* 1994;106–:637–642.

McDonell, TL, et al., A genetic association between juvenile rheumatiod arthritis and a novel interleukin–1α polymorphism. *Arthritis & Rheumatism* 1995;35–221–228.

McGuire, William, et al., Variation in the TNF–α promoter region associated with susceptibility to cerebral malaria. *Nature* 1994;371:508–511.

Mortimore JA, et al., Head trauma as a risk factor for Alzheimer's disease: a collaborative reanalysis of case–control studies. *Eurodem Risk Factors Research Group. Int J. Epidemiol* 1991;20(suppl):S28–35.

Nicklin MJH, et al., A Physical Map of the Region Encompassing the Human Interleukin–1α, Interleukin–1β, and Interleukin–1 Receptor Antagonist Genes, *Genomics* 1994;19:382–384.

Nicoll JA, et al., Apolipoprotein E epsilon 4 allele is associated with deposition of amyloid β–protein following head injury. *Nat Med* 1995;1:2:135–137.

Pociot F, et al., A TagI polymorphism in the human interleukin–1β (IL–1β) gene correlates with IL–1β secretion in vitro. *Eur J Clin Invest* 1992;22:396–402.

Rogaev EI, et al., Familial Alzhemier's disease in kindreds with messense mutuations in a gene on chromosome 1 related to the Alzheimer's disease type 3 gene. *Nature* 1995;376:775–778.

Rogers JT, et al. Translation of the Alzheimer amyloid precursor protein mRNA is up–regulated by Interleukin–1 through 5'–Untranslated Region Sequences. *J Biol chem.* 1999;274:10:6421–6431.

Saunders AM, et al., Association of apolipoprotein E allele ∈4 with late–onset familial and sporadic Alzheimer's disease. *Neurology* 1993;43:1467–1472.

(List continued on next page.)

*Primary Examiner*—Carla J. Myers
*Assistant Examiner*—Alexander H. Spiegler
(74) *Attorney, Agent, or Firm*—Pat Winston Kennedy; Kilpatrick Stockton LLP

(57) ABSTRACT

The present invention provides a method that is useful to predict an individual's increased risk of developing Alzheimer's disease. The method comprises the steps of: (a) collecting a biological sample from an individual; and (b) analyzing the biological sample for the presence of IL-1A 2,2 (−889) genotype, IL-1B 2,2 (+3953) genotype, or a combination of IL-1A 2,2 (−889) and IL-1B 2,2 (+3953) genotypes, the presence of any of the genotypes indicating that the individual is at risk of developing Alzheimer's disease.

9 Claims, 2 Drawing Sheets

OTHER PUBLICATIONS

Sheng JG, et al., In vivo and in vitro evidence supporting a role for the inflammatory cytokine interleukin–1 as a driving force in Alzheimer pathogensis. *Neurolbiology of Aging* 1996;17:761–766.

Sherrington R, et al. Cloning of a gene bearing missense mutuations in early–onset familial Alzheimer's disease. *Nature* 1995;375:754–706.

Verjans, Georges, et al., Polymorphism of the tumor Necrosis Factor Region in Relation to Disease: an Overview. *Spondyloarthropathies* 1992;1:177–186.

Wenham PR, et al., Apolipoprotein E Genotyping by one–stage PCR. *Lancet* 1991;337:1158–1159.

* cited by examiner

METHODS TO IDENTIFY GENETIC PREDISPOSITION TO ALZHEIMER'S DISEASE

This invention was funded in part by grants from the National Institutes of Health (AG124111 and AG10208). The US Government may have certain rights in this invention.

BACKGROUND OF THE INVENTION

Alzheimer's disease (AD), the most common cause of dementia, is estimated to affect 5% of those over 65 years of age and 40% of those over 80 years of age, or a total of approximately 20 million people worldwide. The neuropathological characteristics of AD include: β-amyloid plaques that are diagnostic when associated with dystrophic neurites; neurofibrillary tangles; loss of neurons and synapses; and proliferation of glial cells. The last few years have seen substantial progress in unravelling the genetic influences in AD. A small proportion of AD cases are inherited as an autosomal dominant trait and are attributable to point mutations in genes encoding β-amyloid precursor protein (βAPP),[1] presenilin 1,[2] or presenilin 2.[3] A major genetic risk factor for the much more common sporadic AD is possession of the apolipoprotein E (APOE) e4 allele.[4] However possession of APOE e4 is neither necessary nor sufficient for the development of AD, leaving scope for other potential genetic or environmental influences.

Interleukin-1 (IL-1) is a potent pro-inflammatory cytokine that is markedly overexpressed in Alzheimer brain, predominantly in microglia,[5] suggesting a role for inflammatory processes in AD pathogenesis.[6] This idea has received support from epidemiological studies showing that use of anti-inflammatory agents, in particular non-steroidal anti-inflammatory drugs, is associated with delayed onset or slowed progression of disease.[7] IL-1 has two structurally distinct forms, IL-1a and IL-1β, encoded by separate genes (IL-1 and IL-1B, respectively) located in a cluster on the long arm of chromosome 2 that also includes the IL-1 receptor antagonist gene.[8] Common polymorphisms have been described in both genes and there is evidence that they have functional significance. A polymorphism of the IL-1B gene (+3953), for instance, introduces a Taq1 restriction site resulting in two alleles, designated allele 1 and allele 2.[9] Homozygosity for allele 2 of IL-1B is associated with a fourfold increase in production of IL-1β compared to homozygosity for allele 1.[9] A polymorphism in the 5' regulatory region of the IL-1 gene (a C to T transition at position −889 relative to the start site of transcription) again results in two alleles, also designated allele 1 and allele 2.[10] Both of these IL-1 polymorphisms have been associated with inflammatory diseases. For instance, IL-1 allele 2 has been associated with juvenile rheumatoid arthritis.[10]

Genetic testing is now possible (see U.S. Pat. Nos. 4,582,788, 5,110,920 and 5,686,246) for diseases associated with or caused by one to two genes, once the genes are identified, to determine the risk of a person carrying a given gene for the disease (see for example U.S. Pat. Nos. 4,801,531, 4,666,828, 5,268,267 and 5,686,246). These patents are hereby incorporated by reference into this disclosure.

Many altered physiological functions induce or are caused by inflammatory and other immune mechanisms (see U.S. Pat. No. 5,328,829, column 1, for a review). Due to the commonality of the immune response in almost all disease states, research on inflammatory markers as genetic markers has had very limited success at differentiating predisposition to diseases. U.S. Pat. No. 5,686,246, is a notable exception, in that the inventors correlated IL-1a and IL-1b mutations with the susceptibility to severe periodontal disease.

Association of a single cytokine polymorphism and disease states have been found as, for example, in Systemic Lupus Erythematosus, Ulcerative Colitis and Juvenile rheumatoid arthritis (Mansfield et al., 1994; Verjans et al., 1992; Blakemore et al., 1994; McGuire et al., 1994; McDowell et al., 1995).

Therefore, it was an objective of the present invention to determine if genetic factors that are associated with inflammatory and other immune responses correlate with Alzheimer's disease. If so, it would be useful to identify the genetic factors and thereby identify persons who are susceptible to Alzheimer's disease for the purpose of providing prophylactic treatment.

SUMMARY OF THE INVENTION

It is therefore an object of the present invention to provide methods useful to predict increased risk of Alzheimer's disease development. The method includes investigation of the IL-1A and/or IL-1B banding pattern on a gel, or similar investigation of the genotype at the IL-1A and/or IL-1B locus.

It is a further object to provide kits for determining if a person has a genetic predisposition for Alzheimer's disease development. The kits comprise means for investigating the genotype of an individual at the IL-1A and/or IL-1B locus, and, optionally, other convenient tools which furthers the investigation.

DETAILED DESCRIPTION OF THE INVENTION

Figure 1:
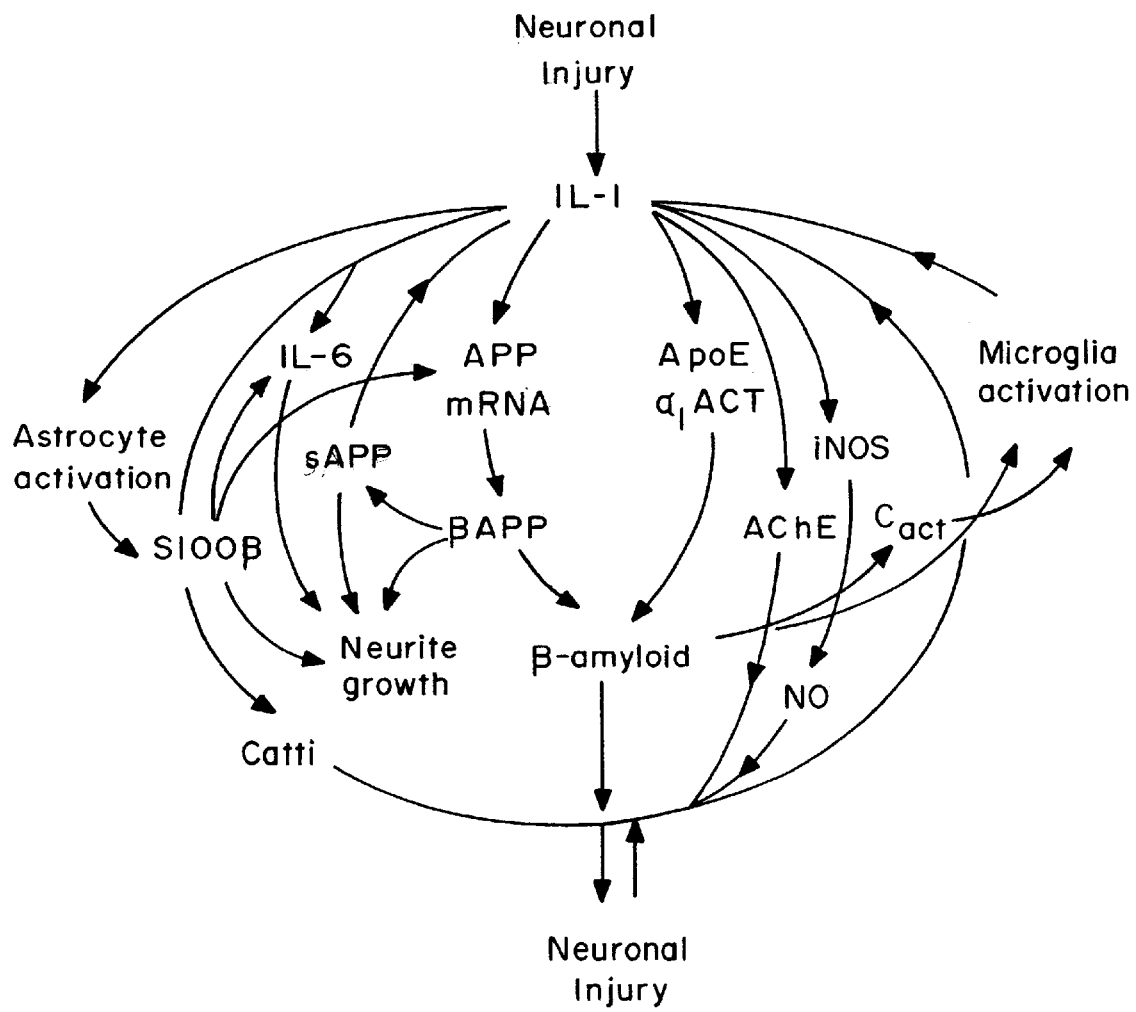
FIG. 1 is a description of the "cytokine cycle"
Figure 2:
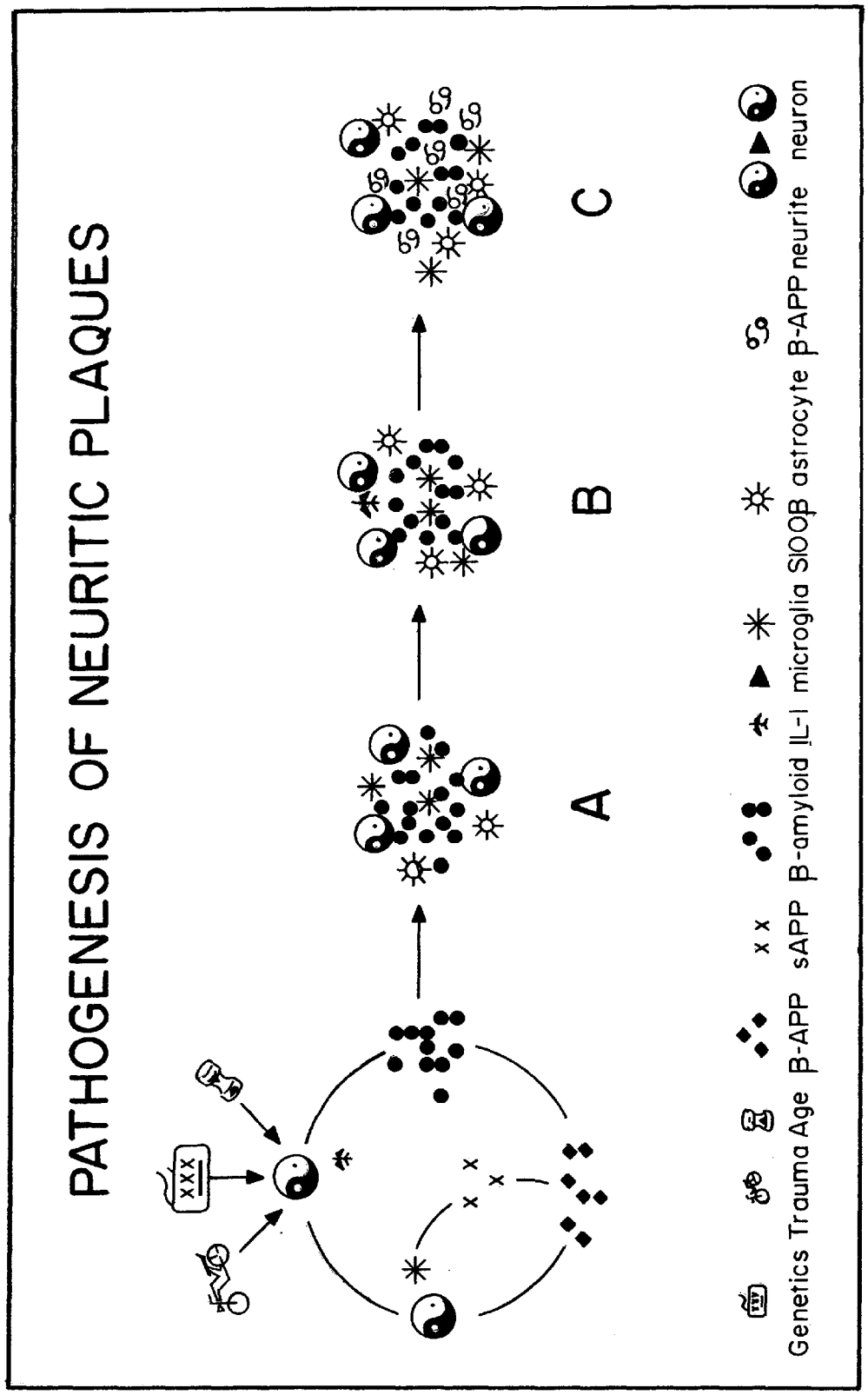
FIG. 2 shows the development of Alzheimer's-associated plaques.

Therefore, the present invention provides methods of determining an individual's increased likelihood of developing Alzheimer's disease, comprising determining if said individual possesses the IL-1A 2,2 genotype, and confirming increased likelihood in the event that the IL-1A 2,2 genotype is present. Preferred are methods as described, wherein said increased likelihood of developing Alzheimer's disease is an increased likelihood of developing earlier-age onset Alzheimer's disease. Those methods wherein the IL-1A 2,2 genotype is a variation at 889 in the promoter region of the IL-1A gene are also preferred. However, those methods wherein said determination is based not only on the possession of the IL-1A 2,2 genotype, but also on possession of the IL-1B 2,2 genotype are most preferred. In the embodiments wherein the IL-1A and IL-1B genotypes are indicative of likelihood, those wherein the IL-1B 2,2 genotype is a variation at +3953 bases distant from the IL-1B promoter that introduces a Taq-1 site is preferred.

In other embodiments of the present invention, there are provided methods of determining an individual's increased likelihood of developing Alzheimer's disease, comprising determining if said individual possesses the IL-1B 2,2 genotype, and confirming increased likelihood in the event that the IL-1B 2,2 genotype is present.

Also provided are methods of determining an individual's likelihood of developing Alzheimer's disease, comprising the steps of:

(a) isolating genomic DNA from the individual;

(b) conducting gel electrophoresis such that any IL-1A 2,2 variations create unique band patterns in the sample and a control; and (c) comparing the band patterns of the individual's sample to a control sample, wherein said control sample comprises an IL-1A 2,2 allele, and wherein the similarity of the genetic polymorphism pattern to the control sample indicates increased likelihood of developing Alzheimer's disease.

Those methods above, wherein the control samples are ethnically matched control samples of known disease history are preferred. Also preferred are those methods wherein said step for identifying in the DNA a genetic polymorphism pattern for IL-1A includes amplification of target DNA sequences using the polymerase chain reaction (PCR) is used. Most preferred are those embodiments discussed in this paragraph wherein said step for identifying in the DNA a genetic polymorphism pattern for IL-1A and IL-1B includes restriction enzyme digestion with restriction enzymes NcoI, TaqI, AvaI and Bsu36I.

Also provided are methods of determining an individual's likelihood of developing Alzheimer's disease, comprising the steps of:

(a) isolating genomic DNA from the individual;

(b) conducting gel electrophoresis such that any IL-1B 2,2 variations create unique band patterns in the sample and a control; and (c) comparing the band patterns of the individual's sample to a control sample, wherein said control sample comprises an IL-1B 2,2 allele and wherein the similarity of the genetic polymorphism pattern to the control sample indicates increased likelihood of developing Alzheimer's disease.

Also provided are methods of determining an individual's likelihood of developing Alzheimer's disease, comprising the steps of:

(a) isolating genomic DNA from the individual;

(b) conducting gel electrophoresis such that any IL-1B 2,2 and IL-1A 2,2 variations create unique band patterns in the sample and a control; and (c) comparing the band patterns of the individual's sample to a control sample, wherein said control sample comprises an IL-1B 2,2 allele and wherein the similarity of the genetic polymorphism pattern to the control sample indicates increased likelihood of developing Alzheimer's disease.

Also provided are methods of determining a individual's likelihood of developing Alzheimer's disease, said method comprising the steps of:

a) isolating genomic DNA from a patient; and b) determining an allelic pattern for IL-1A and IL-1B in the genomic DNA;

wherein the allelic pattern selected from the group consisting of at least one copy of IL-1A 2,2 allele, at least one copy of IL-1B(TaqI) 2,2 allele, and at least one copy of IL-1A 2,2 allele plus at least one copy of IL-1B(TaqI) 2,2 allele indicates increased likelihood of developing Alzheimer's disease.

Kits for predicting an individual's likelihood of developing Alzheimer's disease, said kit comprising means for determining a genetic polymorphism pattern for IL-1A and IL-1B are also provided herein. In particular, kits wherein the means for determining a polymorphism comprises a set of polymerase chain reaction (PCR) primers, which further comprises a control sample comprising IL-1A 2,2 allele and IL-1B (Taq I) allele 2 and which further comprises a means for collecting a DNA sample are provided.

According to the present invention, patients with or without overt disease are identified as having a genetic predisposition for Alzheimer's disease by detecting the presence of a DNA polymorphism in the gene sequence for interleukins IL-1A and/or IL-1B. Alzheimer's disease is understood in the art as that which is defined by CERAD.

The DNA sample may be obtained from blood or tissue samples. In a preferred embodiment, the DNA will be obtained from blood cells obtained from a finger prick of the patient with the blood collected on absorbent paper. In a further preferred embodiment, the blood will be collected on an AmpliCard™. (University of Sheffield, Department of Medicine and Pharmacology, Royal Hallamshire Hospital, Sheffield, England S10 2JF). The DNA is then isolated from the dried blood spots and then target sequences amplified using the polymerase chain reaction (PCR). Oligonucleotide DNA primers that target the specific polymorphic DNA region within the genes of interest are prepared so that in the PCR reaction amplification of the target sequences is achieved. This embodiment has the advantage of requiring only a small amount of blood and avoids the necessity for venipuncture or a tissue biopsy. However, other means for collecting DNA and determining polymorphism patterns as known in the art can be used.

The amplified DNA sequences from the template DNA are then analyzed using restriction enzymes to determine the genetic polymorphisms present in the amplified sequences and thereby provide a genetic polymorphism profile of the individual.

Specific polymorphisms in DNA sequences coding for cytokines IL-1α and/or IL-1β were found to be associated with Alzheimer's disease. These genes map to Chromosome 2; 2q at 12-14.

The alleles of a bi-allelic polymorphism of a single base variation (C/T) at −889 can be identified by allele-specific cleavage using a restriction enzyme. The gene is designated IL-1A while the product (cytokine) is designated IL-1α. Allele 1 is C and allele 2 is T at base −889. The full restriction enzyme recognition site is created by introducing a partial site by mutation in the PCR reaction with a modified primer sequence. The site is completed by the sequence of one of the alleles of the polymorphism. After restriction enzyme digestion of the products of the PCR reaction, the DNA is separated electrophoretically by size.

From this gel (or a southern blot of it probed with a radioactive internal DNA sequence) the alleles of the polymorphism are identified. The uncut fragment (larger) is the rarer allele in Northern European populations.

Two bi-allelic polymorphisms can be typed in two different PCR products using allele-specific cleavage at naturally-occurring sites in the alleles. Allele identification is by size of fragment after restriction digestion and separation in an agarose gel. The gene is designated IL-1B while the product (cytokine) is designated IL-1β. The sites are single base variations (CIT) at −511 (referred to as IL-1B (AvaI)) and at +3953 (referred to as IL-1B (TaqI)) and are identified by allele-specific cleavage using restriction enzymes. For each polymorphism allele 1 is C and allele 2 is T.

The individual's cytokine polymorphism profile, i.e., allelic distribution, can optionally be compared to controls. The controls can be from people who were Alzheimer's free during lifetime, and/or people who had confirmed IL-1A and/or IL-1B mutations. That is, the individual's profile can be compared to healthy people and people with Alzheimer's disease. In one embodiment, controls are provided that are ethnically matched to accommodate genetic variations within subpopulations.

An odds ratio (approximate relative risk) is derived to test the association between allelic polymorphism pattern (genotype) at these specific loci and development of disease and/or its severity. This provides predictive information that will be used in the clinical management of Alzheimer's disease.

The above discussion provides a factual basis for a kit for the identification of a individual's genetic polymorphism pattern associated with increased incidence of Alzheimer's disease. The identification of those at risk for Alzheimer's disease allows preventive measures to be initiated prior to disease onset. The methods used with and the utility of the present invention can be shown by the following example.

EXAMPLES

Case Selection

Tissues and DNA samples from a total of 233 patients with clinical histories of dementia (mean age 81.5 [SD 7.8] years), satisfying standard post mortem neuropathological diagnostic criteria[1,2] for AD were available from four participating centres. Age at death was not recorded in 4 of the cases with AD. 169 aged non-demented controls, mean age 74.4 (SD 9.6) years, without significant AD pathology were available from the same departments.

Genetic Analysis

Genotyping of the IL-1 (−889) and IL-1B (+3953) polymorphisms was performed blind to diagnostic group as described previously. ApoE genotyping was also performed as described previously.[11] IL-1 genotypes could not be determined in 3 cases (one AD and two controls).

Statistical Analysis

Logistic regression analysis was used to assess statistical significance. Univariate analysis was used to identify potential predictors and was followed by a stepwise multivariate analysis to identify increased risk for AD associated with possession of IL-1 allele 2, IL-1B allele 2, both IL-1 allele 2 and IL-1B allele 2, IL-1 2,2 genotype, IL-1B 2,2 genotype, both IL-1 2,2 and IL-1B 2,2 genotypes, after controlling for age, participating centre, and possession of the ApoE e4 allele. Alternative models were developed depending on whether IL-1A alone or both IL-1A and IL-1B are considered; odds ratios quoted are for the development of AD in the presence of the factor relative to its absence.

Results

The IL-1 2,2 genotype is possessed by 12.9% of the AD patients, compared with 6.6% of the controls. For the IL-1B 2,2 genotype the corresponding results are 7.3% and 4.8% respectively. The previously described composite genotype comprising IL-1 allele 2 plus IL-IB allele 2 is present in 36% of AD cases and 30% of controls. Of the 399 patients in the study with complete data, 17 were homozygous for allele 2 of both IL-1 and IL-1B and 15/17 (88%) of these patients had AD. A univariate logistic regression analysis showed that age (p<0.001), possession of ApoE e4 allele (p<0.001), IL-1 2,2 (p=0.03), both IL-1 2,2 and IL-1B 2,2 (p=0.01) genotypes, and participating centre (p=0.03) were significantly associated with AD. A stepwise multivariate analysis showed that each of the following was sufficient to confer increased risk for AD: age, possession of the ApoE e4 allele, possession of the IL-1 2,2 genotype, and possession of the IL-1 2,2 and IL-1B 2,2 genotype No association of AD with participating centre was seen by this analysis, and the relationship of centre with AD in the univariate analysis was attributable to differences in patient age distribution among the different centres. These results, taken together with the role of IL-1 in AD pathogenesis, strongly support a role for these specific IL-1 gene polymorphisms in modulating susceptibility to AD but do not rule out the possibility that these polymorphisms are in disequilibrium with other genes on chromosome 2.

Although the present invention has been fully described herein, it is to be noted that various changes and modifications are apparent to those skilled in the art. Such changes and modifications are to be understood as included within the scope of the present invention as defined by the appended claims.

What is claimed is:

1. A method of determining an individual's risk of developing Alzheimer's disease, comprising the steps of:

(a) collecting a biological sample from an individual; and (b) analyzing the biological sample for the presence of IL-1A 2,2 (−889) genotype, IL-1B 2,2 (+3953) genotype, or a combination of IL-1A 2,2 (−889) and IL-1B 2,2 (+3953) genotypes, the presence of any of the genotypes indicating that the individual is at increased risk of developing Alzheimer's disease.

2. The method of claim 1, wherein the IL-1A 2,2 genotype is a variation at −889 in the promoter region of the IL-IA gene.

3. The method of claim 1, wherein the IL-1B 2,2 genotype is a variation in the coding region at +3953 bases distant from the IL-1B promoter that introduces a Taq-1 site.

4. A method of determining an individual's risk of developing Alzheimer's disease, comprising the steps of:

(a) determining a genetic polymorphism pattern for IL-1A 2,2 (−889), IL-1B 2,2 (+3953), or a combination of IL-1A 2,2 (−889) and IL-1B 2,2 (+3953) in an individual's genomic DNA; and (b) comparing the genetic polymorphism patterns of the individual to a control sample, wherein the control sample comprises an IL-IA 2,2 (−889) allele and an IL-1B 2,2 (+3953) allele, and wherein the identity of the individual's genetic polymorphism pattern compared to the control sample indicates a risk of developing Alzheimer's disease.

5. The method of claim 4, wherein the control sample is ethnically matched to include genetic variations within subpopulations.

6. The method of claim 4, wherein the step of determining a genetic polymorphism pattern for IL-1A 2,2 (−889) and IL-1B 2,2 (+3953) in the individual's genomic DNA includes amplification of target DNA sequences using the polymerase chain reaction (PCR).

7. The method of claim 6, wherein the amplified DNA sequences are analyzed using restriction enzymes NcoI, Taq I, AvaI and Bsu36I.

8. A method of determining an individual's increased risk of developing Alzheimer's disease, comprising the step of:

(a) determining an allelic pattern for IL-IA and IL-1B in an individual's genomic DNA, wherein the allelic pattern of at least one copy of IL-1A 2 (−889) allele, at least one copy of IL-IB 2 (+3953) allele, or at least one copy of IL-1A 2 (−889) allele plus at least one copy of IL-1B 2 (+3953) allele indicates an increased risk of developing Alzheimer's disease.

9. The method of claim 1, wherein the biological sample includes DNA from any tissue.

* * * * *